United States Patent
Stoki

(10) Patent No.: US 6,224,154 B1
(45) Date of Patent: May 1, 2001

(54) OPERABLE CHAIR

(76) Inventor: Stanley R. Stoki, 1340 N. 67$^{th}$ St., Lincoln, NE (US) 68505

( * ) Notice: Subject to any disclaimer, the term of this patent is extended or adjusted under 35 U.S.C. 154(b) by 0 days.

(21) Appl. No.: 09/356,998

(22) Filed: Jul. 20, 1999

(51) Int. Cl.$^7$ .................................................. A61G 15/14
(52) U.S. Cl. .................... 297/339; 297/338; 297/344.18; 297/465
(58) Field of Search ..................... 297/339, 338, 297/344.12, 344.16, 344.18, 344.2, 465, 485

(56) References Cited

U.S. PATENT DOCUMENTS

| | | | |
|---|---|---|---|
| 827,830 | * 8/1906 | Toles | 297/344.18 X |
| 2,193,449 | * 3/1940 | Seversky | 297/344.18 X |
| 2,937,692 | * 5/1960 | McMichael, Jr. | 297/344.16 X |
| 3,116,091 | * 12/1963 | Bethoon et al. | 297/344.18 X |
| 3,625,563 | * 12/1971 | Dickinson | 297/338 X |
| 3,705,745 | * 12/1972 | Ambrousius | 297/344.18 X |
| 4,063,778 | * 12/1977 | Chika | 297/465 |
| 4,186,963 | * 2/1980 | Koutsky | 297/344.18 X |
| 4,254,991 | * 3/1981 | Venieris | 297/344.18 |
| 4,555,138 | * 11/1985 | Hughes | 297/344.18 X |
| 4,738,487 | 4/1988 | Shalinsky et al. | 297/338 |
| 4,889,389 | 12/1989 | White | 297/344.18 X |
| 5,080,191 | * 1/1992 | Sanchez | 297/465 X |
| 5,176,356 | 1/1993 | Lorbiecki et al. | 297/344.18 X |
| 5,186,519 | 2/1993 | Larson | 297/338 X |
| 5,199,763 | 4/1993 | Wilder et al. | 297/338 |
| 5,328,240 | 7/1994 | Neumuller | 297/338 |
| 5,540,403 | 7/1996 | Standley | 297/465 X |
| 5,544,393 | * 8/1996 | McCue et al. | 297/465 X |
| 5,619,949 | 4/1997 | Dick, Jr. | 297/338 X |
| 5,628,548 | 5/1997 | Lacoste | 297/465 X |
| 5,702,158 | 12/1997 | Mengshoel et al. | 297/338 X |
| 5,720,522 | * 2/1998 | Habeck | 297/338 X |

FOREIGN PATENT DOCUMENTS

| | | | |
|---|---|---|---|
| 2229199 | * 12/1974 | (FR) | 297/465 |
| 728849 | * 4/1955 | (GB) | 297/465 |

* cited by examiner

Primary Examiner—Peter M. Cuomo
Assistant Examiner—Rodney B. White
(74) Attorney, Agent, or Firm—Koley Jessen P.C.; Mark D. Frederiksen

(57) ABSTRACT

An operable chair includes a seat which is pivotally connected to a support arm, the support arm being operably mounted on an upright frame for selective vertical movement along the frame. The seat is mounted for selective and adjustable tilting so that an operator may lean forward from the chair at a desired angle. A footrest is operably mounted to the upright support for selective vertical movement there along, independent of the seat. The footrest includes a foot platform which is selectively pivotable as well. A body restraining harness is provided for an operator seated in the seat, and includes an adjustable length cable connected to a bracket operably mounted on the upright support, to adjustably restrain the upper torso of a person seated in the seat, with the upper torso leaning forwardly over a desired work site.

2 Claims, 6 Drawing Sheets

OPERABLE CHAIR

CROSS-REFERENCES TO RELATED APPLICATIONS (Not applicable)

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to vertically operable chairs, and more particularly to an improved operable chair which includes the capability of tilting a seat as well as providing an operable foot support and a separate body harness for supporting the body independently of the seat.

(2) Background Information

The concept of chairs which are capable of vertical movement is well known in the prior art. Such chairs are common in barber shops as well as dental offices, to raise and lower a patient to a position comfortable for the person working on the patient. However, many jobs require an operator to stand for long periods of time at a particular work setting, and in many cases the operator must lean forward over the job site to perform the task. For example, a surgeon must lean over a patient's body for a lengthy period of time during many types of surgery. Thus, even if the surgeon were provided with an operable chair, the need to lean forward over the work site can easily fatigue the surgeon within a short period of time.

Thus, the vertical height of the chair is only one small part of providing an ergonomic environment for a surgeon, or other persons working in a similar environment.

Other features leading to fatigue include:

1. Maintaining the feet in a single position throughout the task;
2. Tilting forward on the edge of a seat to lean over the work environment; and
3. Retaining the upper torso leaning over a patient, or work environment, for a lengthy period of time.

BRIEF SUMMARY OF THE INVENTION

It is therefore a general object of the present invention to provide an improved operable chair which is ergonomic and reduces fatigue for operators sitting in the chair for a long period of time.

A further object of the present invention is to provide an operable chair which includes an operable footrest which may be raised, lowered, and tilted independently of the seat.

Still another object is to provide an improved operable chair with a seat which is vertically movable and tilted independently of the footrest.

Yet another object of the present invention is to provide an improved operable chair which provides a body harness for supporting the upper torso leaning forward out of the seat, to reduce back fatigue.

A further object is to provide an operable chair which is easily moved about a room, is easily operated, and simple to use.

These and other objects will be apparent to those skilled in the art.

The operable chair of the present invention includes a seat which is pivotally connected to a support arm, the support arm being operably mounted on an upright frame for selective vertical movement along the frame. The seat is mounted for selective and adjustable tilting so that an operator may lean forward from the chair at a desired angle. A footrest is operably mounted to the upright support for selective vertical movement there along, independent of the seat. The footrest includes a foot platform which is selectively pivotable as well. A body restraining harness is provided for an operator seated in the seat, and includes an adjustable length cable connected to a bracket operably mounted on the upright support, to adjustably restrain the upper torso of a person seated in the seat, with the upper torso leaning forwardly over a desired work site.

BRIEF DESCRIPTION OF THE SEVERAL VIEWS OF THE DRAWING

The preferred embodiment of this invention is illustrated in the accompanying drawing, in which similar or corresponding parts are identified with the same reference numeral throughout the several views, and in which.

DETAILED DESCRIPTION OF THE INVENTION

Figure 1:
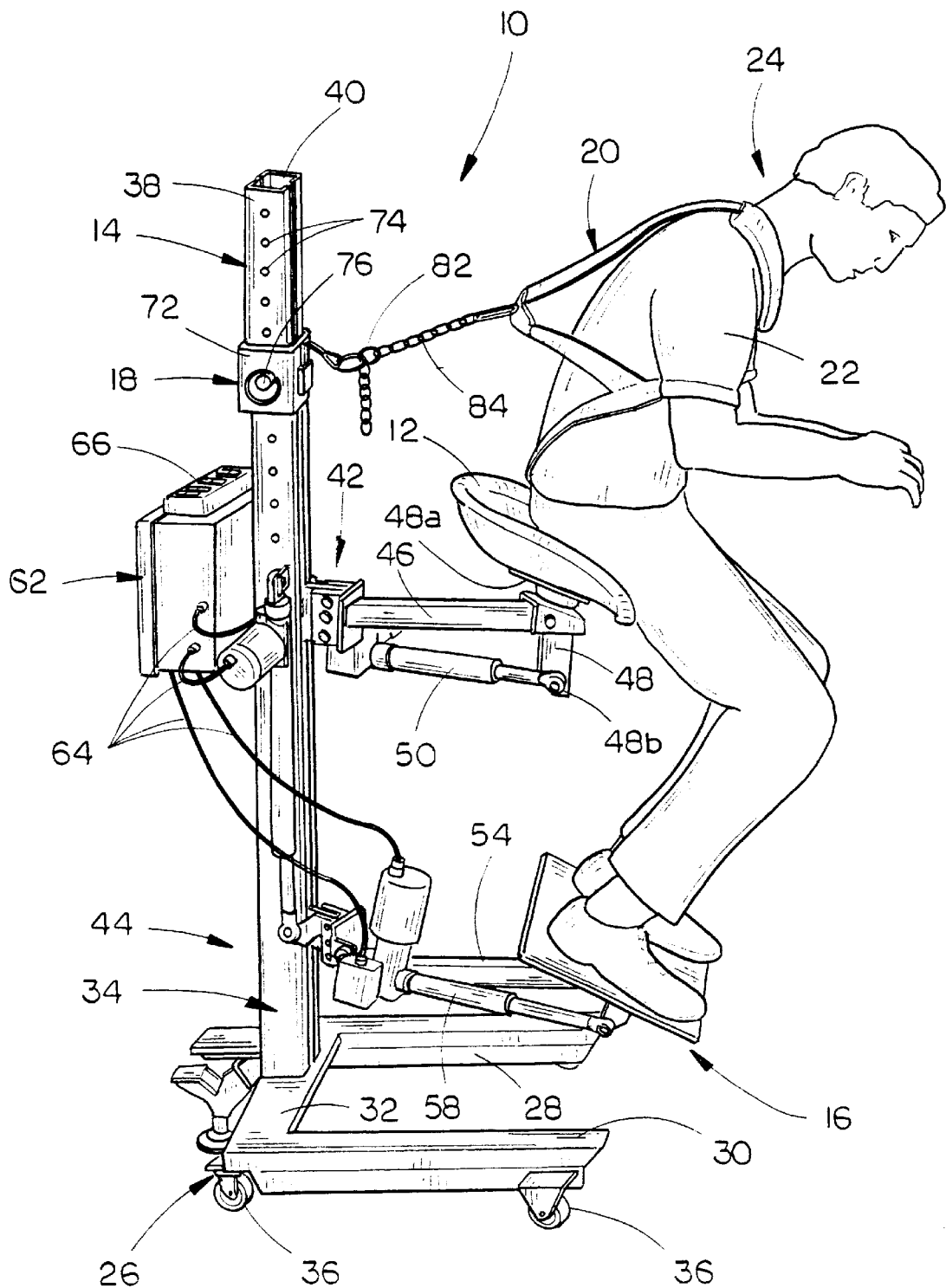
FIG. 1 is a pictorial view of the operable chair of the present invention.

Referring now to drawings, and more particularly to FIG. 1, the operable chair of the present invention is designated generally at 10 and includes a molded seat 12 operably mounted on a portable frame 14 to permit movement of the seat 12 and chair 10 about a room. A foot platform 16 is operably mounted on frame 14 for movement independently of seat 12. A harness bracket 18 is operably mounted on frame 14 independently of seat 12 and foot platform 16, and is selectively connected to a body harness 20 to support the upper torso 22 of an operator 24 seated on seat 12.

Frame 14 includes a U-shaped base 26 having a pair of legs 28 and 30 projecting forwardly from a connector member 32. A mast 34 is mounted centrally on connector 32 between legs 28 and 30, and projects vertically upwardly to support seat 12, foot platform 16, and harness bracket 18.

Preferably, frame 14 has a plurality of wheels 36 mounted on base 26 to permit portability of the frame 14. At least one of wheels 36 is preferably of the type which is selectively lockable, to maintain the frame in the desired position.

Figure 2:
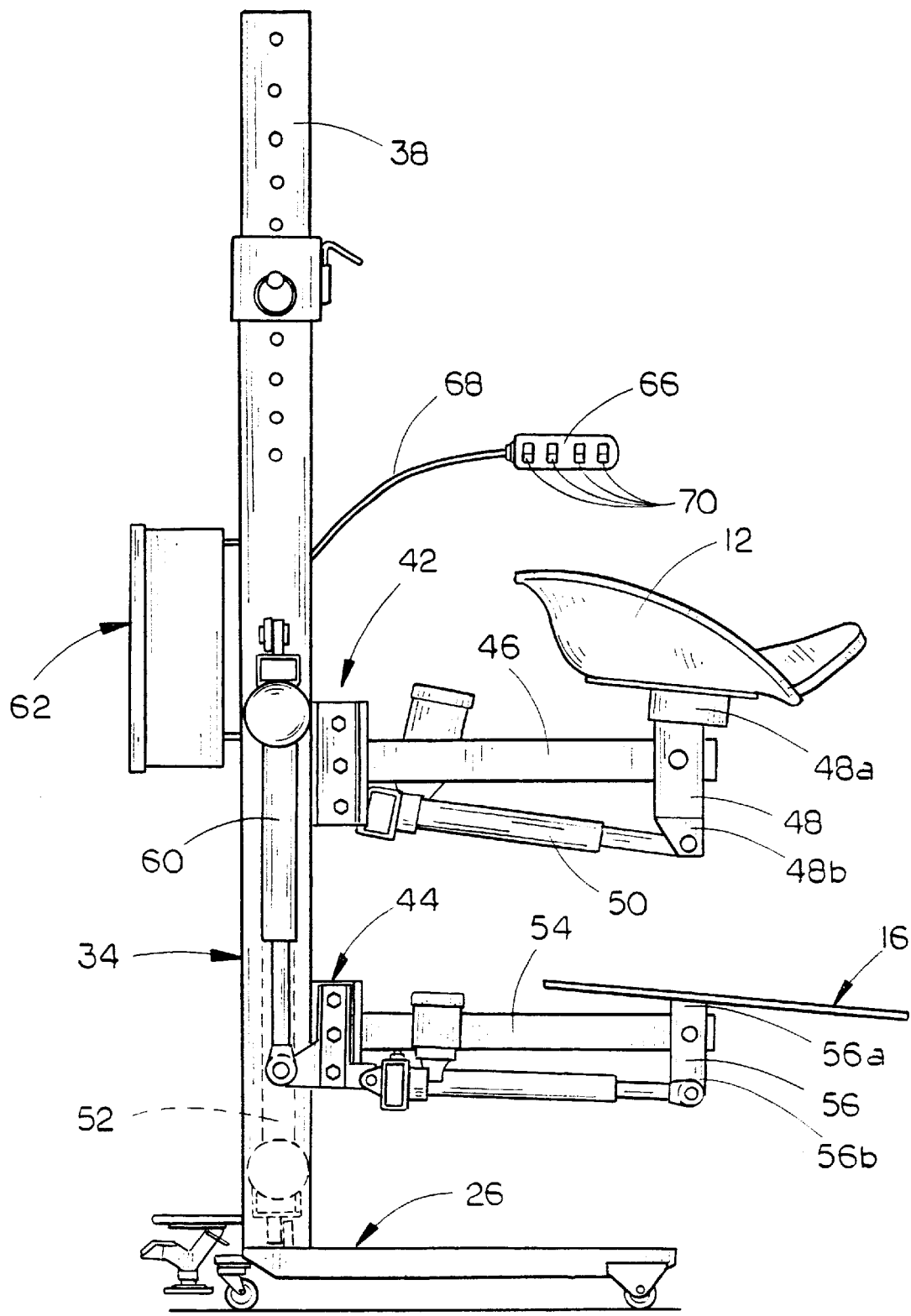
FIG. 2 is a side elevational view of operable chair.
Figure 3:
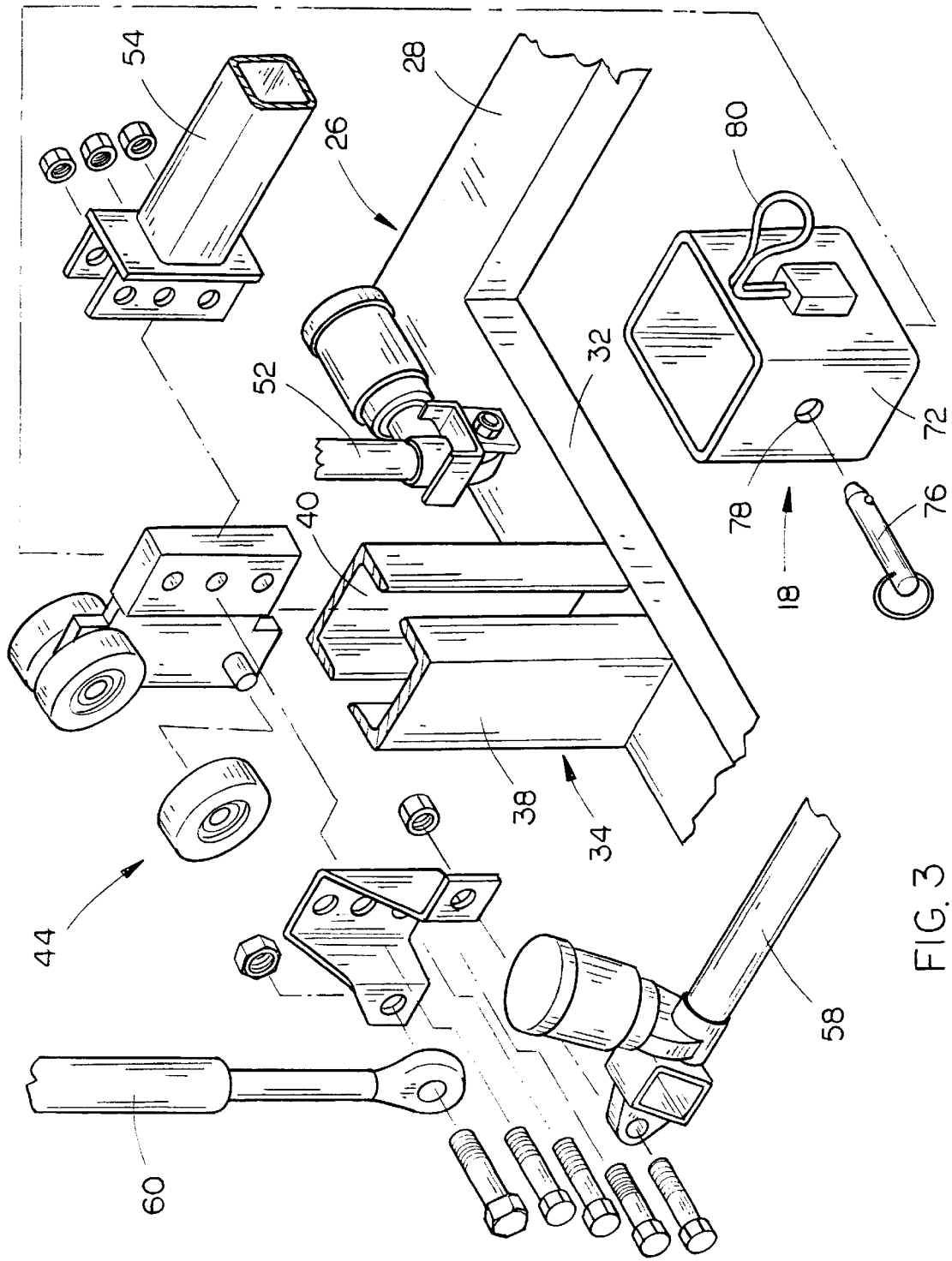
FIG. 3 is an enlarged exploded perspective view of the footrest support arm carriage and its connection to the upright mast.
Figure 4:
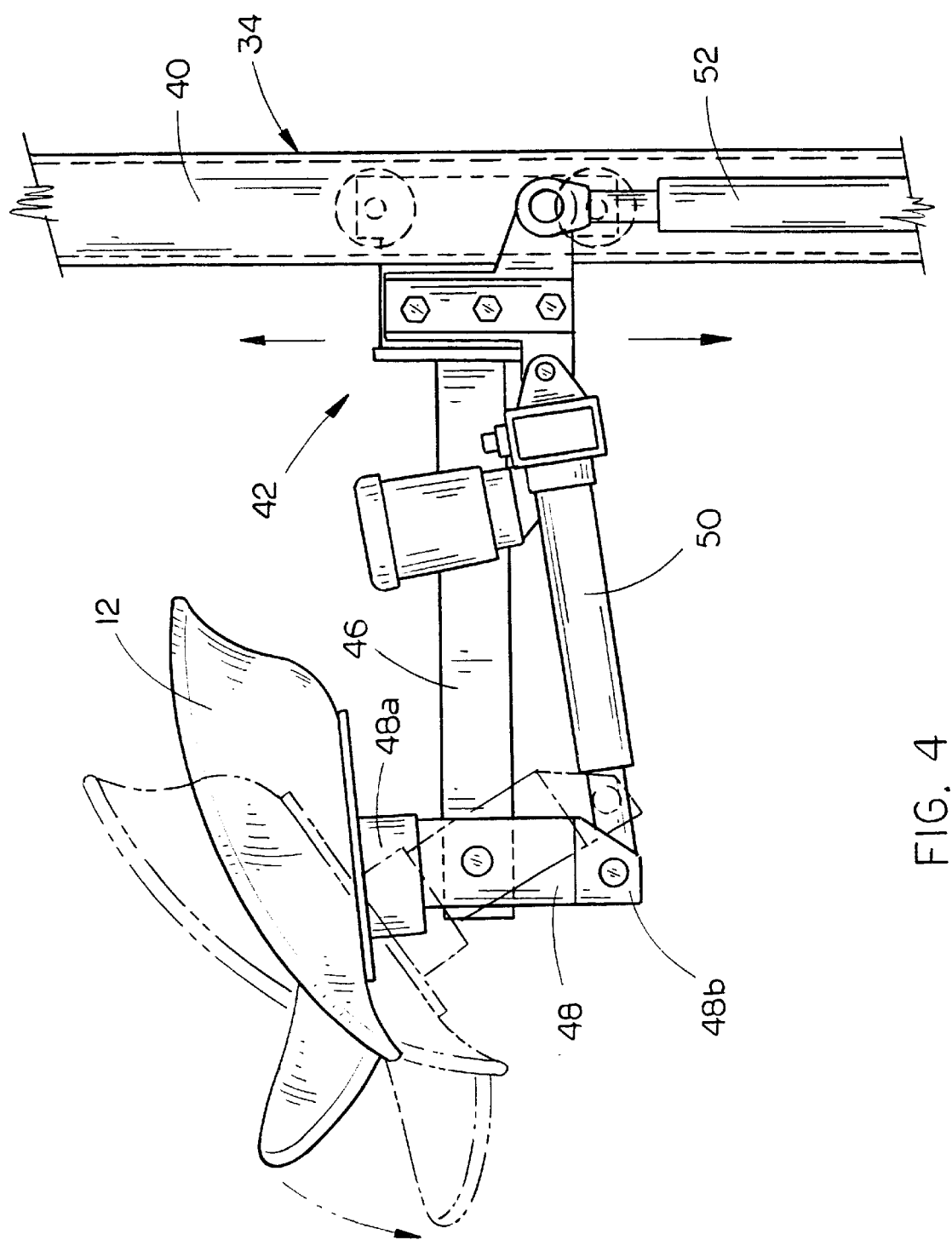
FIG. 4 is a side elevational view of seat and its supporting arm on the mast.

Referring now to FIGS. 1 and 2, mast 34 is preferably formed of a pair of parallel posts 38 and 40. An upper and lower carriage 42 and 44 are operably mounted between the posts, for vertical movement therebetween. This may be accomplished by use of a plurality of rollers or the like, to permit ease of vertical movement. Upper carriage 42 has an arm 46 projecting horizontally forwardly therefrom, for vertical movement with the carriage (see also FIG. 4). A support plate 48 is pivotally connected to the forward end of arm 46, for pivotal movement about a horizontal axis oriented orthogonal to the length of arm 46. Support plate 48 has an upper end 48a projecting upwardly above arm 46 and fastened to the bottom of seat 12. A lower end 48b of support plate 48 projects downwardly below arm 46. A selectively extensible cylinder 50 has one end pivotally mounted to carriage 42 and the other end pivotally connected to the lower end 48b of support plate 48. In this way, cylinder 50 may be activated to pivot support plate 48 on its pivotal axis, and selectively tilt seat 12 between a substantially horizontal position and a forwardly tilted position, as shown in FIG. 4.

An extensible cylinder 52 has an upper end connected to the upper carriage 42 and a lower end connected to frame base 26. Cylinder 52 is operable to selectively raise and lower upper carriage 42 along mast 34, thereby permitting vertical adjustment of seat 12.

Figure 5:
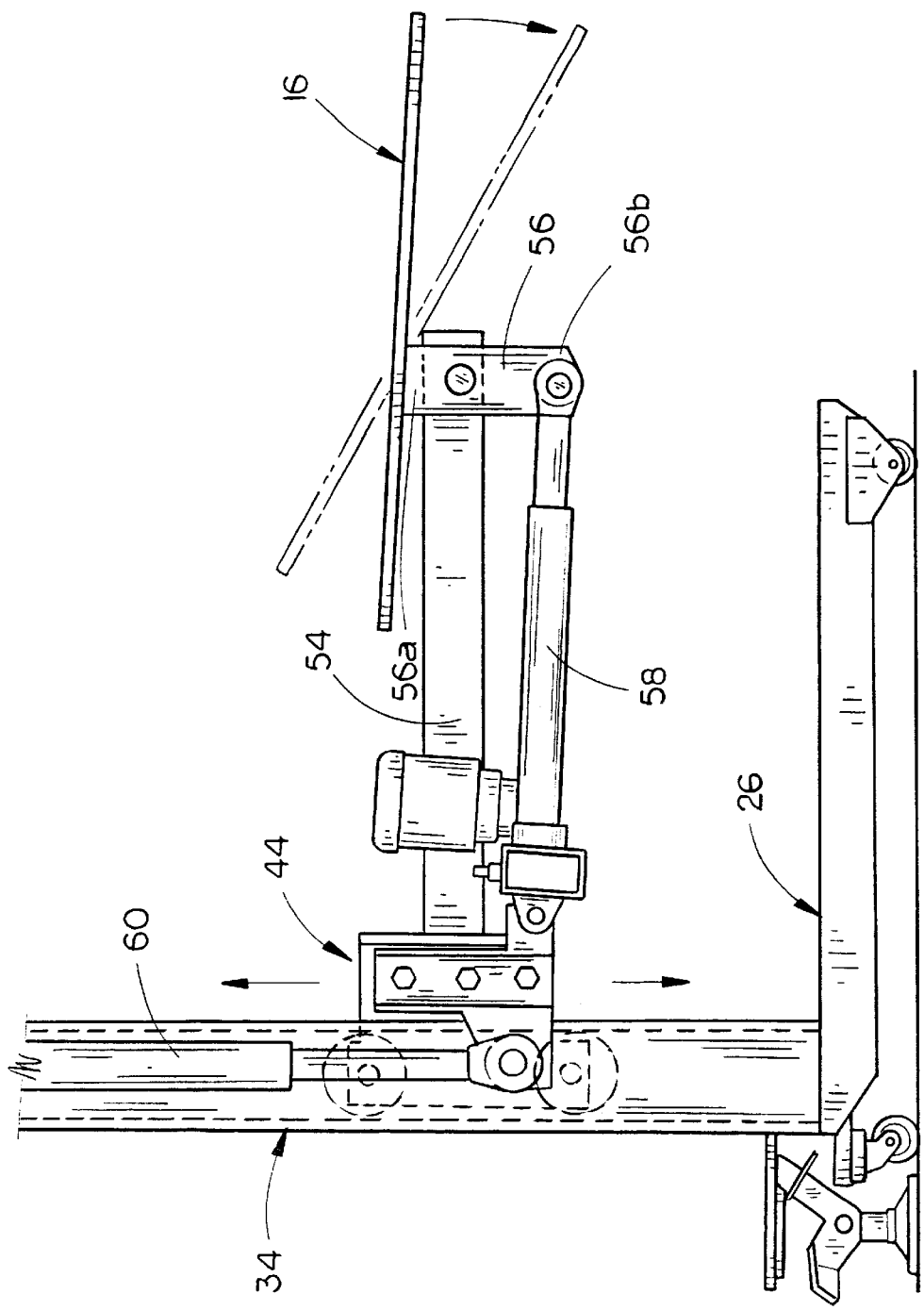
FIG. 5 is a side elevational view of the footrest and its supporting arm on the mast.

Referring now to FIGS. 1, 2, 3 and 5, lower carriage 44 has an arm 54 mounted thereon and projecting forwardly therefrom for vertical movement with lower carriage 44. A lever 56 is pivotally connected to the forward end of arm 54, and has an upper end 56a projecting upwardly beyond arm 54, and a lower end 56b projecting downwardly below arm 54. Foot platform 16 is mounted in a generally horizontal plane orthogonal to and on the upper end 56a of lever 56, for pivotal movement therewith. An extensible cylinder 58 has one end pivotally connected to lower carriage 44, and the opposing end connected to lever lower end 56b. Selective extension and retraction of cylinder 58 will thereby pivot foot platform 16 about a horizontal axis generally orthogonal to arm 54, as shown in FIG. 5.

An extensible cylinder 60 has an upper end connected to mast 34 generally midway along the height of mast 34, and a lower end connected to lower carriage 44. Selective extension and retraction of cylinder 60 thereby selectively raises and lowers lower carriage 44 and the attached foot platform 16.

As shown in FIGS. 1 and 2, a power distribution box 62 is mounted on the rearward side of mast 34, and includes power conduits 64 extending to each of cylinders 50, 52, 58, and 60, for selectively extending and retracting the same. A control box 66 is electrically connected to distribution box 62 via cable 68 and includes independently operable controls 70 for selective activation of each cylinder 50, 52, 58, and 60. Although control box 66 is shown as a hand operable mechanism, it should be understood that the independent operation of the seat and platform controls could be with foot pedals or other equivalent apparatus which is convenient for the operator.

Referring once again to FIG. 1, harness bracket 18 preferably includes a sleeve 72 which is slidably mounted for vertical movement along the upper portion of mast 34. A plurality of vertically aligned and vertically spaced apertures 74 are formed through mast 34 and will selectively receive a pin 76 journaled through a pair of apertures 78 in sleeve 72 (see FIG. 3). In this way, pin 76 will lock bracket 18 at a desired position along mast 34.

A hook or loop 80 is mounted on sleeve 72, and will selectively engage a link 82 of a chain 84. One end of chain 84 is connected to the body harness 20, to thereby support the upper torso of the operator when the operator is leaning forwardly in seat 12. In this way, harness 20 may be supported at a variety of heights and distances from the mast 34.

Figure 6:
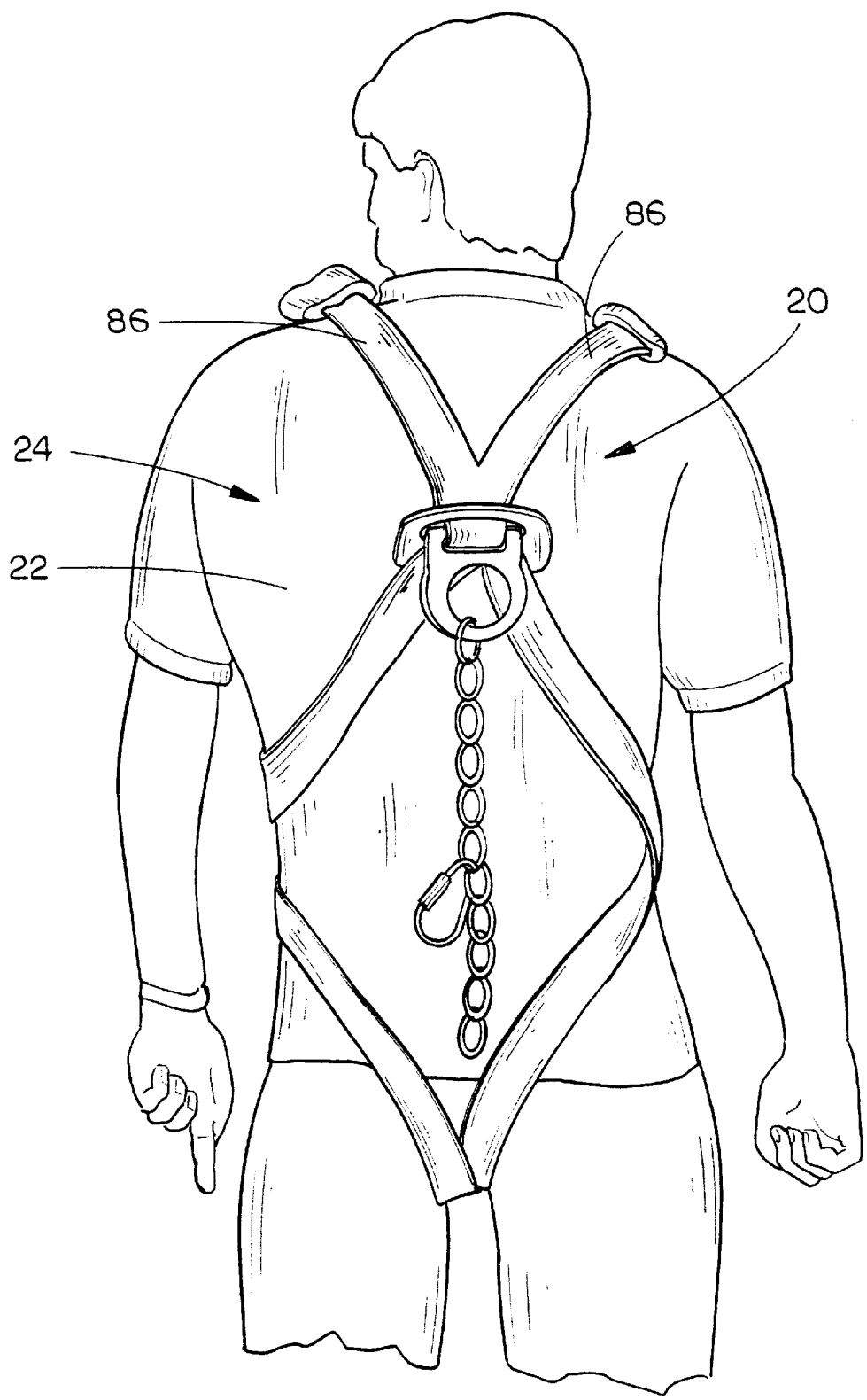
FIG. 6 is a rear elevational view of the body harness of the present invention.

As shown in FIG. 6, harness 20 includes a pair of shoulder straps 86 extending over the shoulders of the operator 24 and then around the sides of the operator's torso to the back, where they are interconnected. A connector strap (not shown) may be used to interconnect shoulder straps 86 across the operator's chest in a conventional fashion. Although harness 20 is shown with straps extending through the operator's legs, these additional lower straps are not absolutely necessary to the invention. Shoulder straps 86 serve to support the upper torso 22 of operator 24 as the operator leans forward over a work site in seat 12.

Whereas the invention has been shown and described in connection with the preferred embodiment thereof, many modifications, substitutions and additions may be made which are within the intended broad scope of the appended claims.

I claim:

1. An operable chair, comprising:

a frame, including a ground supported base and an upright mast;

a first support arm operably connected to the mast for selective vertical movement thereon;

operable means connected between the first arm and the frame for selectively raising and lowering the first arm on the frame;

a seat pivotally connected to the first arm for pivotal movement about a horizontal axis orthogonal to the first arm, and for vertical movement along with the arm; and operable means connected between the seat and the first arm, for selectively pivoting the seat independently of the vertical movement of the seat;

a second support arm operably connected to the mast for selective vertical movement thereon;

operable means connected between the second arm and the mast for selectively raising and lowering the second arm independently of the first arm;

a foot platform mounted on the second arm for movement therewith, for supporting the feet of an operator sitting in the seat;

said foot platform being pivotally mounted on said second arm for pivotal movement about a horizontal axis orthogonal to the second arm;

operable means connected between the foot platform and the second arm for selectively pivoting the foot platform;

a body restraining harness for supporting and restraining the upper torso of a human body;

an adjustable length chain having one end connected to the harness;

means for removably connecting the chain to the frame to retain the harness at a predetermined selectable distance from the frame;

a bracket operably mounted on the frame for selective vertical movement thereon;

means for removably connecting said chain to the bracket;
said harness including:
a pair of shoulder straps for extending over the shoulders of a human body; and
a connector strap connecting the shoulder straps at a location for positioning over the chest of a human within the harness; and a control box including:
- a first controller operably connected to the operable means between the first arm and the frame, for selectively raising and lowering the first arm;
- a second controller operably connected to the operable means connected between the seat and the first arm, for selectively pivoting the seat;
- a third controller operably connected to the operable means connected between the second arm and the frame, for selectively raising and lower the second arm; and
- a fourth controller operably connected to the operable means connected between the foot platform and the second arm, for selectively pivoting the foot platform.

2. The chair of claim 1, further comprising a plurality of wheels operably mounted on the frame for permitting movement of the frame over the ground.

* * * * *